United States Patent [19]
Langer et al.

[11] Patent Number: 6,156,919
[45] Date of Patent: Dec. 5, 2000

[54] PROCESS FOR THE PREPARATION OF ALIPHATIC OLIGOCARBONATE DIOLS FROM DIMETHYL CARBONATE AND ALIPHATIC DIOLS

[75] Inventors: Reinhard Langer, Tönisvorst; Hans-Josef Buysch, Krefeld; Wieland Hovestadt, Leichlingen; Martin Melchiors, Leverkusen, all of Germany

[73] Assignee: Bayer Aktiengesellschaft, Leverkusen, Germany

[21] Appl. No.: 09/461,832

[22] Filed: Dec. 15, 1999

[30] Foreign Application Priority Data

Jan. 9, 1999 [DE] Germany ............... 199 00 554

[51] Int. Cl.$^7$ ................................................. C07C 68/06
[52] U.S. Cl. ................................................. 558/276
[58] Field of Search ............................... 558/276

[56] References Cited

U.S. PATENT DOCUMENTS

| | | | |
|---|---|---|---|
| 2,210,817 | 8/1940 | Peterson | 260/2 |
| 2,787,632 | 4/1957 | Stevens | 260/463 |
| 3,544,524 | 12/1970 | Müller et al. | 260/77.5 |
| 3,631,200 | 12/1971 | Nehring et al. | 260/463 |
| 4,105,641 | 8/1978 | Buysch et al. | 526/712 |
| 4,169,853 | 10/1979 | Knifton | 260/575 |
| 4,201,720 | 5/1980 | Passagne et al. | 260/463 |
| 4,808,691 | 2/1989 | König et al. | 528/76 |
| 5,116,929 | 5/1992 | Greco et al. | 528/44 |
| 5,171,830 | 12/1992 | Grey | 528/371 |
| 5,795,952 | 8/1998 | Greco | 528/196 |
| 5,847,069 | 12/1998 | Greco | 528/196 |

FOREIGN PATENT DOCUMENTS

| | | |
|---|---|---|
| 2349612 | 11/1977 | France . |
| 857948 | 12/1952 | Germany . |
| 196 23 508 | 12/1997 | Germany . |
| 1263225 | 2/1972 | United Kingdom . |
| 1476268 | 6/1977 | United Kingdom . |

*Primary Examiner*—Michael G. Ambrose
*Attorney, Agent, or Firm*—Joseph C. Gil; Thomas W. Roy

[57] ABSTRACT

The present invention relates to a process for the preparation of aliphatic oligocarbonate diols by a) transesterifying dimethyl carbonate with aliphatic diols in the presence of soluble transesterification catalysts in a gas-liquid countercurrent apparatus to form oligocarbonates until the degree of conversion of the initial dimethyl carbonate is more than 80% and b) removing methanol and traces of dimethyl carbonate in an apparatus which generates gas bubbles in the oligocarbonates until the degree of capping of the terminal OH groups with methoxycarbonyl groups is less than 5%.

16 Claims, No Drawings

PROCESS FOR THE PREPARATION OF ALIPHATIC OLIGOCARBONATE DIOLS FROM DIMETHYL CARBONATE AND ALIPHATIC DIOLS

BACKGROUND OF THE INVENTION

1. Field of the Invention

The present invention relates to an improved process for the preparation of aliphatic oligocarbonate diols from non-vicinal diols and dimethyl carbonate (DMC) in a gas-liquid countercurrent apparatus.

2. Description of the Prior Art

Aliphatic oligocarbonates are known as important intermediates, for example, for the manufacture of plastics, lacquers and adhesives, e.g., by reaction with isocyanates. They can be prepared from non-vicinal diols by reaction with phosgene (DE-A 1,595,446), bischlorocarbonic acid esters (DE-A 857,948), diaryl carbonates (DE-A 1,915,908), dioxolanones (DE-A 2,523,352) or dialkyl carbonates (DE-A 2,555,805).

Of the above-mentioned carbonate sources, diphenyl carbonate (DPC) is of particular importance because it can be used to produce aliphatic oligocarbonate diols of particularly high quality (e.g. U.S. Pat. No. 3,544,524, EP-A 292,772).

In contrast to all other carbonate sources, DPC reacts quantitatively with aliphatic OH groups; thus, after the phenol formed has been removed, all the terminal OH groups of the oligocarbonate mixture are available for reaction with isocyanate groups. Also, because only very small concentrations of soluble catalyst are required, it can remain in the product.

Numerous patent applications (e.g. U.S. Pat. No. 2,210,817, U.S. Pat. No. 2,787,632, U.S. Pat. No. 4,169,853, EP-A 364,052) describe the reaction of dialkyl carbonates with aliphatic diols.

The state of the art is to take aliphatic diols together with the catalyst and the dialkyl carbonate and to distil the alcohol formed (ethanol, butanol, allyl alcohol) out of the reaction vessel via a column in such a way that co-vaporized carbonate cannot escape. The reaction is ultimately completed by applying a vacuum to remove unreacted carbonate and residual alcohol. The mixtures are normally only heated and stirred for this purpose.

Despite its good availability, the use of dimethyl carbonate for the preparation of aliphatic oligocarbonate diols has only been known for a short time (U.S. Pat. No. 5,171,830, EP-A 798,327, EP-A 798,328). This can be explained by the low boiling point of DMC and the existence of a low boiling azeotropic mixture with methanol, both of which are an obstacle to the complete conversion of DMC to oligocarbonate diols.

Therefore, these references do not describe processes with high space-time yields and an almost complete reaction of DMC with aliphatic diols to give oligocarbonate diols. The unavoidable occurrence of DMC/methanol mixtures of variable composition appreciably reduces the economic attractiveness of the processes described.

EP-A 798,327 also describes a two-stage process in which initially, with an excess of DMC, an oligocarbonate is produced whose terminal OH groups are in the form of methoxycarbonate groups. Only in a further step, after the addition of another diol and after a total reaction time of 36 hours, is the oligocarbonate diol obtained.

None of these publications considers the practicality of the methods on an industrial scale.

DE-A 19,623,508 describes the transesterification, accelerated by soluble catalysts, of DMC with higher-boiling aliphatic alcohols having only one OH group (monools) in a gas-liquid countercurrent column. To achieve high conversions of DMC (89–99%), it was necessary to accept relatively low conversions of high-boiling alcohol (35 to 58%), suggesting that this technique is unsuitable for the synthesis of high molecular weight oligoesters.

It is an object of the present invention to provide a process for the preparation of oligocarbonate diols by reacting DMC with aliphatic diols, which can be carried out industrially in large, simple apparatus with good space-time yields and a high degree of conversion.

This object may be achieved with the process according to the present invention by carrying out the reaction of dimethyl carbonate and aliphatic diols in the presence of soluble catalysts in a gas-liquid countercurrent apparatus, followed by the separation of residual methanol and traces of dimethyl carbonate in an apparatus which generates gas bubbles in the oligocarbonate.

SUMMARY OF THE INVENTION

The present invention relates to a process for the preparation of aliphatic oligocarbonate diols by a) transesterifying dimethyl carbonate with aliphatic diols in the presence of soluble transesterification catalysts in a gas-liquid countercurrent apparatus to form oligocarbonates until the degree of conversion of the initial dimethyl carbonate is more than 80% and b) removing methanol and traces of dimethyl carbonate in an apparatus which generates gas bubbles in the oligocarbonates until the degree of capping of the terminal OH groups with methoxycarbonyl groups is less than 5%.

DETAILED DESCRIPTION OF THE INVENTION

It accordance with the present invention the aliphatic oligocarbonate diols can be prepared with a degree of capping of the terminal OH groups by methoxycarbonyl groups of less than 5%, preferably less than 1%, by reacting dimethyl carbonate with aliphatic diols at a degree of conversion of the initial dimethyl carbonate of more than 80%, preferably more than 90%, more preferably more than 95% and most preferably more than 98%.

Examples of gas-liquid countercurrent apparatus which can be used are known and include bubble-cap columns with 2 to 20 plates, optionally with a relatively large liquid hold-up, or bubble column cascades with 2 to 8, preferably 2 to 4, bubble columns. Several bubble columns without baffles may be replaced by one column with baffles to prevent back-mixing.

Another gas-liquid countercurrent apparatus which can be used is a tank cascade with 2 to 6, preferably 2 to 3, tanks that are preferably equipped with gas distribution stirrers.

In the countercurrent apparatus the process according to the invention is carried out at temperatures between 100 and 250° C., preferably between 150 and 200° C., and at pressures between 0.8 and 8 bar, preferably between 1 and 4 bar.

Suitable soluble catalysts are known and include transesterification catalysts, especially alkali metal and alkaline earth metal hydroxides and metal alcoholates of aliphatic alcohols having 1 to 8 carbon atoms with metals of groups IA, IIA, IIIA and IVA (main groups), IIB and IVB (subgroups) or the rare earth metals of Mendeleev's periodic table of the elements. It is preferable to use sodium and potassium alcoholates or titanium and zirconium alcoholates. The titanium and zirconium tetraalcoholates are preferably used with diols containing ester groups.

Examples of transesterification catalysts include sodium methylate, potassium methylate, sodium hydroxide, potassium hydroxide, titanium tetraisopropylate and zirconium tetraisopropylate.

The catalyst concentrations used in the process according to the invention are 0.001 to 1%, preferably 0.005 to 0.5% and more preferably 0.02 to 0.2%. These percentages are based on the weight of metal in the catalyst and are based on the weight of the aliphatic diol.

As the apparatus which generates gas bubbles in the oligocarbonate, it is possible to use a bubble column cascade or a tank cascade, preferably with gas distribution stirrers. The apparatus which generates gas bubbles may also be integrated into the gas-liguid countercurrent apparatus. The apparatus, which generates gas bubbles in the oligocarbonate, is operated at a temperature of 150 to 250° C., preferably 170 to 220° C., and at a pressure of 0.01 to 1 bar, preferably 0.05 to 0.5 bar.

For products of medium and small annual tonnage, the process according to the invention is preferably carried out as a semibatch process with a large bubble column or a large tank, preferably with a gas distribution stirrer, into which the dimethyl carbonate is metered and in which the demethoxylation ultimately takes place, and with an attached bubble-cap column, small tank cascade or bubble column cascade, in which the countercurrent transesterification takes place. The liquid volume of the countercurrent part of the plant is 0.5 to 50%, preferably 1 to 25% and more preferably 2 to 12%, of the volume of the large tank.

In accordance with the present invention it is possible to produce oligocarbonate diols which contain 30 to 300, preferably 60 to 200 and more preferably 100 to 150 carbon atoms, and correspond to the formula:

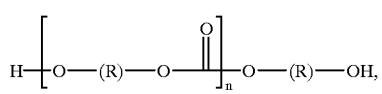

wherein
  R represents an aliphatic radical containing 3 to 50, preferably 4 to 40 and more preferably 6 to 30 carbon atoms and optionally ester, ether, amide or nitrile groups, and
  n is an integer of 2 to 30, preferably 3 to 20 and more preferably 3 to 15.

Suitable aliphatic diols for preparing the oligocarbonate diols of formula (I) include pentane diol, hexane diol, neopentyl glycol, cyclohexane dimethanol, the addition products (esterdiols) of caprolactone with these alcohols, and mixtures of these diols. It is preferred to use ester diols, such as those obtained by using caprolactone and hexane diol. It is also possible to use mixtures of caprolactone with these said diols and form the esterdiols in situ.

The apparatus which generates gas bubbles is an important part of the process according to the invention. The gas bubbles are produced by introducing inert gases (such as nitrogen, argon, methane, ethane, propane, butane, dimethyl ether, dry natural gas or dry hydrogen) into the apparatus which generates gas bubbles. It is possible for part of the gas stream leaving the oligocarbonate, and containing methanol and dimethyl carbonate, to be recycled into the oligocarbonate in order to saturate it.

The gas bubbles can also be produced by introducing inert, low boiling liquids, such as pentane, cyclopentane, hexane, cyclohexane, petroleum ether, diethyl ether or methyl tert.-butyl ether. It is possible for the substances to be introduced in liquid or gaseous form and for part of the gas stream leaving the oligocarbonate, and containing methanol and dimethyl carbonate, to be recycled into the oligocarbonate in order to saturate it.

The substances for producing gas bubbles are preferably introduced into the oligocarbonate by means of annular nozzles or gas distribution stirrers, it being preferable to use annular nozzles for bubble columns and gas distribution stirrers for stirred tanks.

One embodiment of an industrial plant for the production of oligocarbonate diols can be constructed as follows: A 10 m³ tank with a DMC inlet tube extending to the bottom, and with a gas distribution stirrer, can be connected either to a vacuum pump via a condenser with receiver for low boiling liquids, or to a 4-stage bubble column cascade with a pressure retaining valve, downstream condenser and receiver for low boiling liquids. The tank and each of the bubble columns can be heated. Each bubble column has a liquid volume of 100 liters. The bubble columns are connected in series in such a way that the gas stream from the tank and the mixture of aliphatic diol and catalyst are conveyed countercurrently. The tank can be operated at an overpressure of up to 3 bar with the bubble column cascade or at an absolute pressure of up to 50 mbar with the vacuum unit. The gas distribution stirrer of the reaction tank can be operated either with fresh gas, or with gas from the tank space, or with mixtures of these gases.

A semibatch production can be carried out as follows: The tank and bubble columns are placed under nitrogen and are heated to the reaction temperature. The metering of the diol/catalyst mixture is started. The mixture is fed into the uppermost bubble column. When this column is completely full, the mixture flows on to the next and finally into the tank. When the tank is sufficiently full for the gas distribution stirrer to be immersed in the liquid, the metering of the DMC is started, the gas distribution stirrer is switched on and the pressure retaining valve is set to the desired pressure. The condensate leaving the reactor, and containing methanol and a small amount of DMC, has its composition analyzed and the amount of DMC to be metered in is corrected by the amount not taken up.

After the calculated amount of diol/DMC has been pumped in, the connection between the tank and the bubble column cascade is closed and the connection to the vacuum pump is opened. The application of a slight vacuum starts the distillation of the low-boiling liquids; the gas distribution stirrer is operated with tank gas. When the distillation rate drops, the vacuum is increased until it reaches 150 mbar. As the distillation rate drops, the gas feed to the gas distribution stirrer is converted to an inert compound, e.g. nitrogen. From time to time the tank contents can be analyzed for residual bound methanol. After the degree of capping has fallen below a stipulated value, the system is ventilated with nitrogen and the tank contents are cooled; a complexing agent for the catalyst used is optionally stirred in, or the acid catalyst is neutralized, or the tank contents are worked up for the separation of catalyst.

The semibatch procedure described is only an example of one embodiment of the present invention and should not be used to limit the scope of the invention. It is within the skill in the art to convert such a process to a fully continuous process.

The process according to the invention allows for the production of high quality oligocarbonate diols from DMC with good space-time yields, high DMC conversions and a low degree of capping of the terminal OH groups.

The oligocarbonates prepared by the process according to the invention can be used, e.g., for the manufacture of plastics, fibers, adhesives or coatings. They can also be used as binders, binder constituents and/or reactive thinners in solventless and low solvent polyurethane coatings. They are suitable as raw materials for moisture-curable coatings and as raw materials and/or binder components in solvent-based and aqueous polyurethane coatings. They can also be used as raw materials for polyurethane prepolymers containing free NCO groups, and as raw materials for preparing polyurethane dispersions.

The oligocarbonate diols prepared by the process according to the invention can also be used for the manufacture of thermoplastics, such as aliphatic and/or aromatic polycarbonates and thermoplastic polyurethanes.

EXAMPLES

The percentages for the compositions of the distillates obtained are in mole %, while the percentages for compounds in the bottom phases and the catalyst contents of the aliphatic diols are wt. %. NL/h means liter per hour (l/h) at
T=20° C. and
p=1 bar
=$10^5$ Pa

Example 1
Potassium alcoholate-catalyzed transesterification of DMC with hexane diol in a continuous transesterification column The apparatus was a 20-plate oil-thermostatted bubble-cap column with an internal diameter of 5 cm and a liquid hold-up of approx. 850 ml. At the gas outlet, the column had a thermostatted dephlegmator and at the liquid outlet the column had an oil-heated gravity-return evaporator with a liquid capacity of approx. 70 ml.

The column was thermostatted with a stream of heat-transfer oil at 120° C.

The dephlegmator was heated with oil at 80° C. and the gravity-return evaporator was heated with oil at 180° C.

The column was operated at ambient pressure.

640 ml per hour of a mixture of hexane diol and 0.28% of potassium hydroxide, at 120° C., were pumped onto the uppermost column plate by means of a metering pump. A gaseous stream of dimethyl carbonate at 120° C. was simultaneously introduced between the column and the gravity-return evaporator. This gas stream was produced by vaporizing 330 ml of dimethyl carbonate per hour.

The molar ratio of DMC to hexane diol fed into the column was 1 to 1.25.

The gas stream leaving the dephlegmator was condensed and collected to give 275 to 285 ml/h of liquid. Gas chromatographic analysis showed that this liquid was made up of 99.986% of methanol and 0.014% of hexane diol. The dimethyl carbonate content was below the detection limit of 0.01%.

Approx. 712 g/hr of a colorless liquid substance were removed from the evaporator. Gas chromatographic analysis of this mixture showed that it contained approx. 4% of unbound methanol, 0.7% of dimethyl carbonate and 7.4% of unreacted hexane diol.

Example 2
Sodium alcoholate-catalyzed transesterification of DMC with hexane diol in a continuous transesterification column Example 1 was repeated except that the hexane diol stream contained 0.14% of sodium hydroxide instead of potassium hydroxide.

The gas stream leaving the dephlegmator was condensed and collected to give 276 to 280 ml/h of liquid. Gas chromatographic analysis showed that this liquid was made up of 99.98% of methanol and 0.02% of hexane diol. The dimethyl carbonate content was below the detection limit of 0.01%.

Approx. 710 g/hr of a colorless liquid substance were removed from the evaporator. Gas chromatographic analysis of this mixture showed that it contained approx. 4.5% of unbound methanol, 0.7% of dimethyl carbonate and 8.0% of unreacted hexane diol.

Example 3
Sodium alcoholate-catalyzed transesterification of DMC with hexane diol in a continuous transesterification column with a very high space-time yield Example 2 was repeated except that three times the amount of DMC and hexane-diol/sodium hydroxide mixture was fed into the column.

The gas stream leaving the dephlegmator was condensed and collected to give approx. 840 ml/h of liquid. Gas chromatographic analysis showed that this liquid was made up of 99.928% of methanol and 0.045% of hexane diol. The dimethyl carbonate content exceeded the detection limit at 0.027%. Approx. 2150 g of a colorless liquid substance were removed per hour from the evaporator. Gas chromatographic analysis of this mixture showed that it contained approx. 5.9% of unbound methanol, 1.0% of dimethyl carbonate and 9.5% of unreacted hexane diol.

Example 4
Sodium alcoholate-catalyzed transesterification of DMC with an equimolar mixture of hexane diol, neopentyl glycol and cyclohexane dimethanol in a continuous transesterification column The experimental apparatus of Example 1 was heated to 140° C. and the dephlegmator and gravity-return evaporator were at temperatures of 80° C. and 220° C., respectively. 645 ml per hour of an equimolar mixture of hexane diol, neopentyl glycol and cyclohexane dimethanol, at 140° C., were pumped onto the uppermost column plate. The mixture contained 0.1% of sodium hydroxide. A gas stream at 140° C., produced by vaporizing 205 ml of DMC per hour, was introduced simultaneously. The molar ratio of diol to DMC was approx. 2.1 to 1.

The gas stream leaving the dephlegmator was condensed and collected to give approx. 190 ml/h of liquid. Gas chromatographic analysis showed that this liquid had the following composition: 99.84% of methanol, 0.04% of DMC, 0.10% of neopentyl glycol and 0.02% of cyclohexane-dimethanol. The hexane diol content of the distillate was below the detection limit.

Approx. 660 g of a colorless liquid substance were removed per hour from the evaporator. Gas chromatographic analysis of this mixture showed that it contained approx. 0.7% of unbound methanol, 0.04% of dimethyl carbonate, 3.8% of unreacted hexane diol, 4.4% of unreacted neopentyl glycol, 3.5% of unreacted cyclohexanedimethanol and 3.6% of neopentyl glycol carbonate.

Example 5
Sodium alcoholate-catalyzed transesterification of DMC with hexane diol in a semibatch tank with a 10-plate countercurrent column The apparatus consisted of a 5 l flat-flange pot with vane stirrer, flow spoilers and inlet tube; a 10-plate oil-heated bubble-cap column with dephlegmator; and a total condenser for the gas leaving the column. The column had a liquid hold-up of approx. 170 ml.

The column and tank were heated to 160° C. and rendered completely inert with nitrogen. The dephlegmator was thermostatted at 80° C.

940 ml (9.2 mol) per hour of hexane diol containing 0.14% of sodium hydroxide, at 160° C., were pumped onto the uppermost plate.

After 860 ml (6.92 mol) of hexane diol/sodium hydroxide mixture had been pumped onto the plate, the stirrer was switched on and 780 ml (9.2 mol) per hour of dimethyl carbonate were introduced through the inlet tube into the liquid at the bottom of the tank. The metered addition was adjusted after three hours.

A total of 1475 g of distillate having the following composition was formed in this time: 99.2% of methanol, 0.6% of dimethyl carbonate and 0.2% of hexane diol.

4456 g of a colorless liquid containing 3.4% of methanol, 1.1% of DMC and 4.2% of unreacted hexane diol were found in the bottom flask.

Volatile constituents were then drawn off through the column at 120° C. and 20 to 40 mbar. After 3 hours the methanol content had dropped to 0.1%. Dimethyl carbonate was no longer detectable. The blowing of 40 Nl per hour of nitrogen through the inlet tube was then started at normal pressure; the column was replaced with an off-gas tube for this purpose. In 3 hours the methanol content dropped to 400 ppm, after which 60 Nl per hour of nitrogen were introduced for 2 hours at 140° C. Methanol could not be detected by gas chromatography.

A particularly sensitive gas chromatographic headspace analysis, performed before and after saponification with aqueous KOH, showed 45 ppm of free methanol and 35 ppm of bound methanol. Therefore, the degree of capping of the terminal OH groups was below 0.05%.

Example 6

Sodium alcoholate-catalyzed elimination of methanol from the oligocarbonate of Example 4

4 l of oligocarbonate from Example 4 were placed in the 5 l tank of Example 5 and volatile constituents were then drawn off at 120° C. and 20 to 40 mbar via a cold trap. After 3 hours the methanol content had dropped to 1000 ppm. Dimethyl carbonate was no longer detectable. The blowing of 40 Nl per hour of nitrogen through the inlet tube was then started at normal pressure. In 3 hours the methanol content dropped to 450 ppm, after which 60 Nl per hour of nitrogen were introduced for 2 hours at 140° C. Methanol could then no longer be detected by gas chromatography.

A particularly sensitive gas chromatographic headspace analysis, performed before and after saponification with aqueous KOH, showed 40 ppm of free methanol and 32 ppm of bound methanol. Therefore, the degree of capping of the terminal OH groups was below 0.05%.

Examples 7–9

Titanium alcoholate-catalyzed transesterification of DMC with an oligomer mixture prepared from hexane diol and caprolactone, in a semibatch tank with a 10-plate countercurrent column The apparatus consisted of a 5 l flat-flange pot with vane stirrer, flow spoilers and inlet tube, a 10-plate oil-heated bubble-cap column with dephlegmator, and a total condenser for the gas leaving the column. The column had a liquid hold-up of approx. 170 ml.

The column and tank were heated to 200° C. and rendered completely inert with nitrogen. The dephlegmator was thermostatted at 80° C.

An equimolar mixture of hexane diol and caprolactone containing 1% of titanium tetraisopropylate was prepared; this corresponds to a titanium content of 0.14%.

1392 g per hour of the product of hexane diol and caprolactone containing 0.14% of titanium, at 160° C., was pumped onto the uppermost plate.

After 464 g of diol had been pumped onto the plate, the stirrer was switched on and 540 g of DMC per hour were introduced through the dip tube into the liquid at the bottom of the tank. After 10 minutes the metering was adjusted to 928 g of DMC and 2386 g of diol mixture per hour for a further 70 minutes. Metering was then returned to the original pumping rates for 10 minutes.

A total of approx. 880 g of distillate, consisting of approx. 85% of methanol and 15% of dimethyl carbonate, was obtained in this time.

The bottom contains 1.93% of methanol.

Dimethyl carbonate, hexane diol and caprolactone were not detectable.

Because of the unreacted dimethyl carbonate in the distillate, a further 223 g of dimethyl carbonate were subsequently metered in over 25 minutes to give a further 164 g of a distillate consisting of 94% of methanol and 5.6% of DMC.

200 Nl per hour of nitrogen were then introduced through the inlet tube into the flat-flange pot. After nitrogen had been introduced for 4 to 5 hours, 300 ppm of bound methanol were found. This amount dropped to approx. 40 ppm after 6 to 7 hours, corresponding to a degree of capping of the terminal OH groups of approx. 0.25%.

The aliphatic oligocarbonate formed was pale yellowish in color.

When 100 Nl of nitrogen were introduced through the dip tube instead of 200 Nl, about 12 to 14 hours were required to reduce the bound methanol content to approx. 40 ppm.

Approx. 21 to 22 hours were required when 50 Nl of nitrogen were introduced.

Examples 10–11

Titanium alcoholate-catalyzed transesterification of DMC with an oligomer mixture prepared from hexane diol and caprolactone, in a semibatch tank with a 10-plate countercurrent column, followed by stripping with inert gas under reduced pressure The apparatus described in Example 7 was converted so that, by operating a valve, the column could be isolated from the flat-flange pot and instead connected via cold traps to a vacuum pump so that the pressure could be regulated. The nitrogen flow was adjusted via a flux regulator and kept constant.

The experimental conditions were as described in Examples 7 to 9 up to the point of stripping with nitrogen.

When the introduction of DMC had ended, the column was isolated by closing the valve and the vacuum unit, set to a constant suction pressure of 150 mbar, was connected.

From this point the nitrogen stream was introduced through a dip tube with the following stepwise gradient: up to 1 hour, no nitrogen was introduced; 1 to 2 hours: 2 Nl/h; 2 to 7 hours: 20 Nl/h; 7 to 12 hours: 40 Nl/h; and 12 to 17 hours: 90 Nl/h.

By introducing gas through a simple dip tube, a bound methanol content of 66 ppm was reached after 17 hours.

The introduction of gas through a 3 cm long glass frit gave a bound methanol content of 45 ppm after only 12 hours.

Examples 12–13

Titanium alcoholate-catalyzed transesterification of DMC with an oligomer mixture prepared from hexane diol and caprolactone, in a semibatch tank with a gas distribution stirrer and a 10-plate countercurrent column, followed by stripping with inert gas under reduced pressure The apparatus described in Example 7 was converted so that, by operating a valve, the column could be isolated from the flat-flange pot and instead connected via cold traps to a vacuum pump so that the pressure could be regulated. The nitrogen flow was adjusted via a flux regulator and kept constant.

The flat-flange pot was equipped with a gas distribution stirrer having two outlets for introducing gas into the tank contents.

The gas incorporated into the liquid phase could either originate from the tank itself or could be introduced from outside as a defined gas stream.

The gas distribution stirrer speed was approx. 850 rpm.

Up to the point of stripping with nitrogen, the experimental conditions were as described in Examples 10 and 11 except that the gas distribution stirrer very efficiently incorporated the tank's gas phase into the liquid phase.

By using the gas distribution stirrer, the amount of distillate dropped to approx. 700 g and was made up of approx. 95% of methanol and 5% of dimethyl carbonate.

The bottom contained 2.16% of methanol. Dimethyl carbonate, hexane diol and caprolactone were not detectable.

Because of the unreacted dimethyl carbonate in the distillate, a further 77 g of dimethyl carbonate were subsequently metered in over 9 minutes to give an additional approx. 57 g of a distillate made up of 98.2% of methanol and 1.8% of DMC.

When the introduction of DMC ended, the column was isolated by closing the valve and the vacuum unit, set to a constant suction pressure of 150 mbar, was connected.

From this point the nitrogen stream was introduced through the dip tube with the following stepwise gradient: up to 1 hour: no nitrogen was introduced; 1 to 2 hours: 2 Nl/h; and 2 to 7 hours: 20 Nl/h.

By introducing gas through a simple dip tube with the gas distribution stirrer running at the same time, a bound methanol content of 68 ppm was reached after only 7 hours.

When nitrogen was introduced via the gas distribution stirrer, which in that case was disconnected from the tank gas space, a bound methanol content of 40 ppm was reached after only 6 hours with a continuous nitrogen flow of 2 Nl per hour.

Example 14

Comparative experiment with vacuum stripping and without the generation of gas bubbles Experiment 10 was repeated except that, after application of the vacuum of 150 mbar, the mixture was stirred without nitrogen being introduced. After 8 hours a residual methanol content of approx. 4000 ppm could be detected. The methanol content dropped to approx. 1000 ppm after 24 hours.

The space-time yield would drop markedly if the batch size were increased to an industrial scale of several m$^3$.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing an aliphatic oligocarbonate diol by
    a) transesterifying dimethyl carbonate and an aliphatic diol in the presence of a soluble transesterification catalyst in a gas-liquid countercurrent apparatus to form an oligocarbonate until the degree of conversion of the initial dimethyl carbonate is more than 80% and
    b) removing methanol and traces of dimethyl carbonate in an apparatus which generates gas bubbles in the oligocarbonate until the degree of capping of the terminal OH groups with methoxycarbonyl groups is less than 5%.

2. The process of claim 1 wherein the gas-liquid countercurrent apparatus is a bubble-cap column with 2 to 20 plates.

3. The process of claim 1 wherein the gas-liquid countercurrent apparatus used is a bubble column cascade with 2 to 8 bubble columns.

4. The process of claim 1 wherein the gas-liquid countercurrent apparatus used is a tank cascade with 2 to 6 tanks.

5. The process of claim 4 wherein said tanks are equipped with gas distribution stirrers.

6. The process of claim 1 wherein the countercurrent apparatus is operated at a temperature of 100 to 250° C. and a pressure of 0.8 to 8 bar.

7. The process of claim 1 wherein the soluble catalyst comprises an alkali metal hydroxide, an alkaline earth metal hydroxide or an alcoholate of a Group IA, IIA, IIIA, IVA, IIB, IVB or a rare earth metal.

8. The process of claim 1 wherein a bubble column cascade or a tank cascade with gas distribution stirrers is used as the apparatus which generates gas bubbles in the oligocarbonate.

9. The process of claim 8 wherein the apparatus which generates gas bubbles in the oligocarbonate is operated at a temperature of 150 to 250° C. and a pressure of 0.01 to 1 bar.

10. The process of claim 1 which comprises conducting step a) in a large tank equipped with a gas distribution stirrer and conducting step b) in an attached bubble-cap column, small tank cascade or bubble column cascade, wherein the liquid volume of the apparatus used for step b) is 0.5 to 50% of the volume of the large tank.

11. The process of claim 1 wherein the oligocarbonate corresponds to the formula:

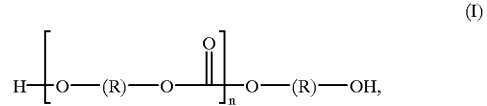

(I)

wherein

R represents an aliphatic radical containing 3 to 50 carbon atoms and optionally containing ester, ether, amide or nitrile groups and n is an integer from 2 to 30.

12. The process of claim 1 wherein said aliphatic diol comprises pentane diol, hexane diol, neopentyl glycol, cyclohexanedimethanol or the reaction product of caprolactone with one of these alcohols.

13. The process of claim 1 which comprises producing gas bubbles in the apparatus which generates gas bubbles by introducing an inert gas.

14. The process of claim 13 wherein said inert gas comprises nitrogen, argon, methane, ethane, propane, butane, dimethyl ether, dry natural gas or dry hydrogen.

15. The process of claim 1 which comprises producing gas bubbles in the apparatus which generates gas bubbles by introducing an inert low boiling liquid.

16. The process of claim 15 wherein said inert low boiling liquid comprises pentane, cyclopentane, hexane, cyclohexane, petroleum ether, diethyl ether or methyl tert.-butyl ether.

* * * * *